United States Patent [19]

Cornell et al.

[11] 4,425,235

[45] Jan. 10, 1984

[54] BLOOD COLLECTION DEVICE WITH PHASE PARTITIONING MEANS

[75] Inventors: William D. Cornell, Ballwin; Joel Joslin, St. Louis, both of Mo.

[73] Assignee: Sherwood Medical Company, St. Louis, Mo.

[21] Appl. No.: 360,706

[22] Filed: Mar. 22, 1982

[51] Int. Cl.³ ............... B01D 17/00; B01D 21/26
[52] U.S. Cl. .................. 210/516; 210/789; 210/927; 422/101
[58] Field of Search ........... 210/927, 516, 789, 518, 210/800, 804; 422/101

[56] References Cited

U.S. PATENT DOCUMENTS

| | | | |
|---|---|---|---|
| 3,852,194 | 12/1974 | Zine | 210/83 |
| 3,909,419 | 9/1975 | Ayres | 210/516 |
| 3,920,549 | 11/1975 | Gigliello | 210/83 |
| 3,929,646 | 12/1975 | Adler | 210/927 |
| 3,957,654 | 5/1976 | Ayres | 210/516 |
| 3,976,579 | 8/1976 | Bennett | 210/516 |
| 3,986,962 | 10/1976 | Kessler | 210/927 |
| 4,021,340 | 5/1977 | Zine | 210/83 |
| 4,046,699 | 9/1977 | Zine | 210/789 |
| 4,055,501 | 10/1977 | Cornell | 210/516 |
| 4,088,582 | 5/1978 | Vabilisetti et al. | 210/516 |
| 4,189,382 | 2/1980 | Zine | 210/46 |
| 4,246,123 | 1/1981 | Cornell et al. | 210/782 |
| 4,315,892 | 2/1982 | Stone et al. | 422/101 |

*Primary Examiner*—Steven L. Weinstein
*Attorney, Agent, or Firm*—Stanley N. Garber; Gregory E. Upchurch; William R. O'Meara

[57] ABSTRACT

A blood collection device for collecting and separating whole blood into its relatively low and high density phases includes a collection container, and a housing having an enlongate passageway in the housing. Gel-like material having a specific gravity intermediate the specific gravities of the separated high and low density phases is disposed in the passageway. A piston having a specific gravity greater than that of the gel-like material is disposed in the passageway and sized to allow gel-like material to flow past it at a low flow rate and to retard the movement of the piston during centrifugation of the device. Means for preventing the flow of the gel-like material from the housing and toward the interface of the phases until the piston has moved out of the passageway is provided.

17 Claims, 7 Drawing Figures

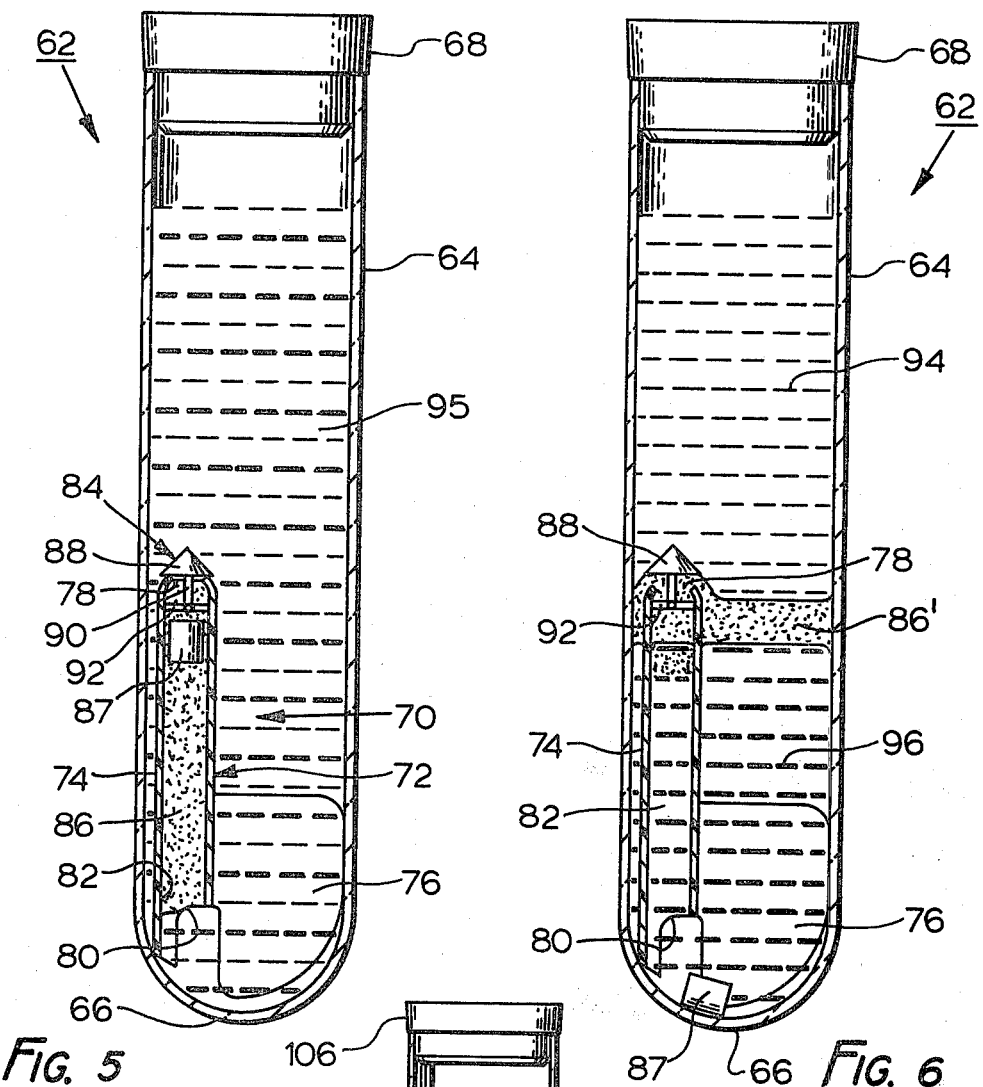
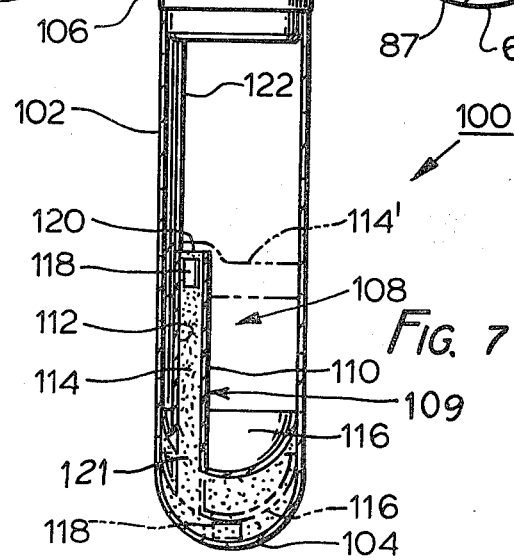

4,425,235

BLOOD COLLECTION DEVICE WITH PHASE PARTITIONING MEANS

DESCRIPTION

TECHNICAL FIELD

This invention relates to blood collection devices having phase partitioning means and more particularly to such devices in which the partitioning means includes thixotropic gel-like material flowable to the blood phase interface during centrifugation of the device.

BACKGROUND ART

In blood sample testing it is well known to employ thixotropic gel-like materials in evacuated blood collection tubes to automatically obtain phase separation and a phase partition or barrier between the separated blood phases (serum or plasma and the cellular phase) during centrifugation of the blood filled tube. Such gel-like materials may include a mixture of silicone and a silicon dioxide powder such as disclosed in U.S. Pat. No. 3,852,194. In U.S. Pat. No. 4,021,340 a mixture of liquid polybutene polymer and silicon dioxide powders are used to form a partitioning material. The gel-like material is made to have a specific gravity intermediate the specific gravities of the separated phases so that the material moves during centrifugation to the phase interface to form a phase barrier between the separated phases. The phase barrier maintains the phases separated during storage or shipment, and until the low density phase, serum or plasma, is decanted or otherwise removed for clinical analysis.

In U.S. Pat. No. 4,246,123 and U.S. application, Ser. Nos. 31,817, now abandoned, filed Apr. 20, 1979, housings having standpipes or passages are used to convey the gel-like material toward the interface. In this way, the gel-like material flows from the bottom of the collection tube through the passageway and cellular phase without contacting the cellular phase. This tends to reduce hemolysis due to gel/cell collision, prevent gel material from trapping cells, and reduce the chance of trapping red blood cells in the lower density phase.

In U.S. Pat. No. 4,315,892, a valve is employed at the upper end of a standpipe in the low density phase zone of the collection tube. The standpipe is filled with gel-like material. The movable member of the valve has a specific gravity greater than the specific gravity of the low density (about 1.03) phase so that it will eventually be actuated to the open position, but is less than that of whole blood (about 1.05) so that the valve does not open immediately or too soon. When the specific gravity of the liquid decreases sufficiently below the specific gravity of the movable valve member, the valve member moves downwardly opening outlet ports in the standpipe and allowing gel-like material to flow from the standpipe to the interface of the separated phases. The valve provides a time delay permitting the barrier to be formed after phase separation has taken place and independently of the viscosity of the gel-like material and speed of the centrifuge. However, the driving force necessary to actuate the valve is relatively small since it depends on a relatively small specific gravity difference between the valve member and the liquid adjacent the member. Thus, in some cases, friction and inertia of parts can undesirably affect the operation of the valve.

DISCLOSURE OF THE INVENTION

It is therefore an object of the present invention to provide an improved blood phase collection device incorporating means for delaying the flow of phase partitioning gel-like material which is positive in operation and wherein one or more of the above described disadvantages of the prior art are overcome.

In accordance with one aspect of the present invention, a blood collection device is provided which includes a container for receiving a blood sample and a blood phase partitioning device in the container. The partioning device includes a housing having an elongated passageway carrying thixotropic gel-like partitioning material and time delay means for delaying the initiation of the flow of the gel-like material. The time delay means includes a movable member in the passageway having a specific gravity greater than that of the gel-like material. The movable member is sized relative to the passageway so that during centrifugation, movement of the movable member is retarded as it moves along the passageway. The time delay means includes means for preventing the gel-like material from flowing until the movable member moves beyond the opposite end of the passageway.

These objects, as well as other objects and advantages of the present invention, will become apparent from the following detailed description and drawings.

BRIEF DESCRIPTION OF THE DRAWINGS

FIG. 5 is an elevational view in cross-section of a blood collection device in accordance with a modified embodiment of the present invention, the container of the device being shown with a sample of blood;

FIG. 6 is an elevational view in cross-section of the blood collection device of FIG. 5 but after complete phase separation and formation of a phase partition; and FIG. 7 is an elevational view in cross-section of still another embodiment of the present invention.

DETAILED DESCRIPTION OF THE PREFERRED EMBODIMENTS

Figure 1:
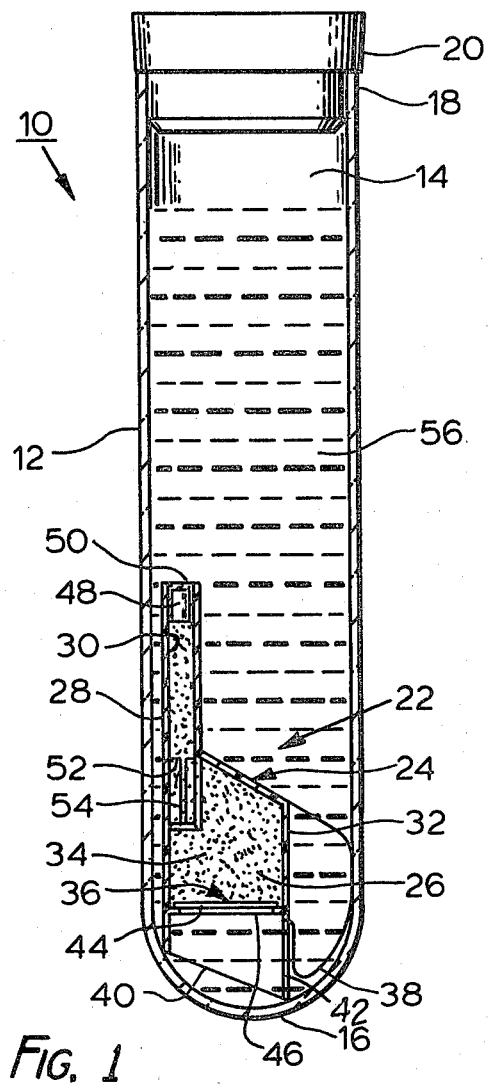
FIG. 1 is an elevational view in cross-section of a blood collection device in accordance with a preferred embodiment of the present invention and shown with a blood sample filling the device.
Figure 2:
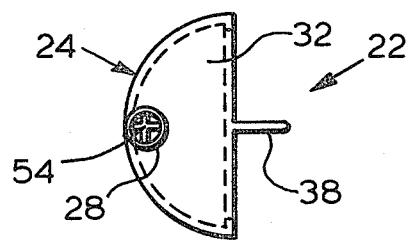
FIG. 2 is a top-plan view of the phase partitioning device of FIG. 1.

Referring now to the drawings, and particularly to FIGS. 1-4, there is shown a blood collection device 10 adapted to receive a sample of whole blood for the purpose of separating and partitioning it into its relatively low and high density phases. The device 10 includes a blood collection container or tube 12, for example, of glass, which has a blood collection chamber 14 closed at the bottom, for example, by an integral container bottom end portion 16. Container 12 has an open upper end 18 that is closed by a stopper 20. Disposed in chamber 14 of the collection container 12 is a fluid or blood phase partitioning device indicated generally at 22.

The stopper 20 may be a conventional elastomeric or rubber stopper which is piercable by a needle cannula for introducing blood into chamber 14 and which is self-sealing at the site of penetration when the needle is removed from the stopper. Preferably, the chamber 14, during manufacture of the device 10, is provided with a predetermined negative pressure or vacuum with the stopper maintaining the negative pressure in the chamber until the device is used. Evacuation of tube 12 of course facilitates the introduction of the blood sample into the tube.

The phase partitioning device 22 includes a housing 24 filled with thixotropic gel-like partitioning or barrier forming material 26. Housing 24 includes an elongate vertically extending tube or pipe 28 having an internal vertically extending passageway 30. Housing 24 has a lower enlarged portion 32 providing a barrier material reservoir 34. The reservoir 34 is normally closed by a normally closed valve 36 normally preventing fluid communication between the liquid sample or blood in the tube 12 and the gel-like material in reservoir 34. Housing 24 also includes a stabilizing fin 38 and a bottom end extension 40 which engage the inner walls of tube 12. The extension 40 has a cut out or opening 42 which ensures flow of liquid to the bottom of the reservoir 34 and one side of the valve 36. Valve 36 includes a movable valve member 44 illustrated as a separate, flat plate or cover normally covering a valve passage or opening 46 in the reservoir 34.

Partitioning device 22 further includes a movable member shown as piston 48 initially disposed adjacent the upper open end or outlet 50 of passageway 30. The bottom open end of passage 30 is indicated at 52 and is connected to a cage 54 which, as will be further described, receives and retains the piston 50 during centrifugation of the device 10.

The gel-like material 26 may be any well-known phase barrier material, for example, it may be one made by mixing silicone or a liquid polymer with a powder or powders to form a thixotropic gel-like material. As is well known, by properly choosing and proportioning the silicone or polymer liquid and the powder, the desired specific gravity and viscosity can be obtained. Such thixotropic gel-like materials are substantially water insoluble and inert to the components of blood. They are made to have a specific gravity intermediate the specific gravities of the low density serum or plasma which is about 1.03 and the relatively high density cellular phase which is about 1.09. The gel-like material is generally prepared to have a specific gravity between about 1.035 and 1.06 and is preferably about 1.04 or 1.045. The gel-like material 26, when at rest and under normal handling and shipping conditions, is semi-solid or non-flowable, but when subjected to forces such as centrifugal forces occurring during phase separation, the gel-like material becomes flowable. Upon cessation of the centrifugal forces the gel-like material returns to its semi-solid or substantially non-flowable state to provide a substantially permanent liquid-impervious barrier between the separated phases.

The housing 24 is maintained at the bottom of tube 12 such as by a suitable friction fit with the tube walls and/or may be formed of a material such that the housing alone has a specific gravity greater than that of the cellular phase so that the cellular phase does not tend to move the housing 24 upwardly from its normal position at the bottom of the tube 12 during centrifugation of the device 10. It may be held in place by other suitable means where desired. Housing 24 may be made or molded as a single part from a suitable plastic such as polyethylene or polypropylene mixed with a filler, such as barium sulfate or a metal powder of the like, in order to obtain the desired specific gravity. The specific gravity of the flat valve member 44 is not too critical and may be about that of the cellular phase or less.

The specific gravity of piston 48 is made greater than the specific gravity of gel material 26. Preferably, it is made substantially greater than that of the gel-like material and that of the high density phase of blood, for example, it may be made of aluminum and have a specific gravity such as about 2.7, more than twice that of the gel-like material and cellular phase. By having a relatively high specific gravity, good driving forces, that is, forces tending to move the piston downwardly during centrifugation of the device are relatively high so that the piston cannot "hang up" or get stuck, and the characteristics of the flow of gel will generally be the same in each device manufactured. The piston 48 in passage 30 acts as a time-delay in the operation of the partitioning device 22, that is, it serves to delay the initiation of the flow of the gel-like material 26 from housing 24 for a predetermined time after the start of the centrifuge, as will be discussed hereafter.

In use, a sample of blood may be drawn into chamber 14 of container 12 by using a double-ended needle cannula such as provided by a conventional needle holder and tube guide. For example, after the distal end of the cannula is inserted into the vein of a patient, the device 10 is moved onto the proximal end of the cannula until the cannula pierces stopper 20, whereupon whole blood flows into container 12. The filled container is subsequently placed in a centrifuge such that the lower end 16 will be radially outwardly of the stopper 20 and the axis of the rotation of the centrifuge during centrifugation. As is well known, if it is desired to separate serum, a blood clot is formed before centrifuging the device. For example, glass particles may be provided in tube 12 to aid coagulation. On the other hand, where plasma is desired, an anti-coagulant may be placed in the tube during manufacture to prevent clotting. In FIG. 1, the tube 12 is shown filled by a selected amount of whole blood indicated at 56. During centrifugation of device 10, the high density cellular phase, including the clot in the case of serum separation, will move toward the bottom end 16 while the lower density phase, serum or plasma, will move toward the upper portion of tube 12. After the centrifuge has started, piston 48, having a higher specific gravity than that of gel-like material 26, will move downwardly in passage 30 pressurizing the gel-like material in passage 30 and that in reservoir 34. The piston 48 is sized relative to the width or diameter of passage 30 such that gel-like material flows past the piston at only a low rate of flow as the piston moves downwardly toward the lower end 52 of passage 30. The pressurization of gel-like material 26 during this time causes a pressure differential across piston 48 and valve member 44 in a direction to maintain the valve 36 closed and no gel-like material can flow out of outlet 50 and into the interior of the tube 12. In this case, the pressure of the gel-like material on the top or inner side of valve member 44 will be greater than the pressure of the cells acting on the bottom side of valve member 44. During this time, of course, the cellular phase is moving toward the bottom end 16 of tube 12.

Figure 4:
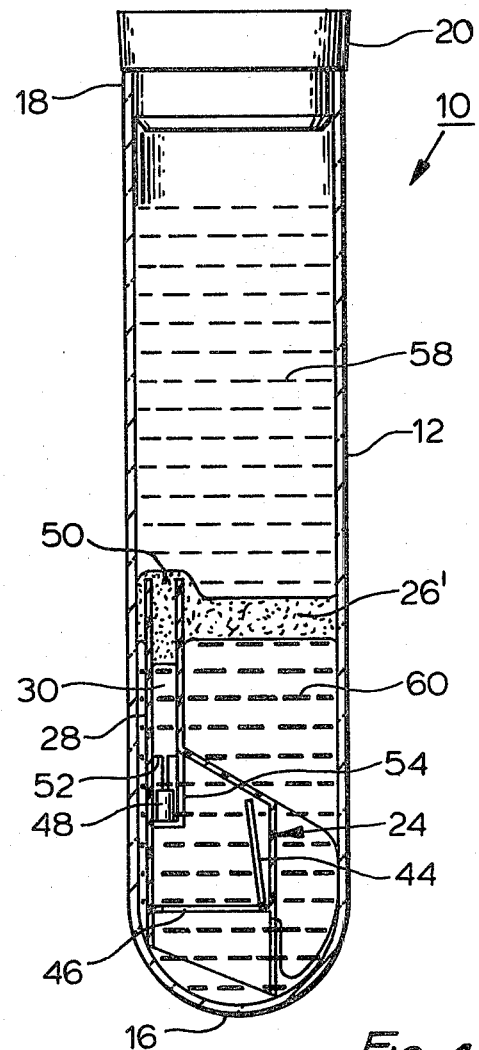
FIG. 4 is an elevational view in cross-section of the blood collection device of FIG. 1 but shown after the sample of blood has been centrifuged to separate the phases and to provide a phase partition of gel-like material between the phases.
Figure 3:
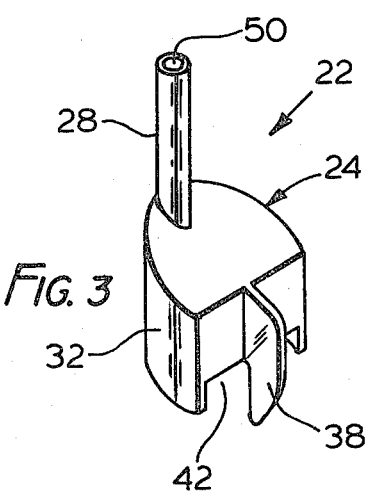
FIG. 3 is a perspective view of the phase partitioning device of FIG. 1.

During further centrifugation of device 10, the piston 48 continues to move downwardly in passage 30, maintaining valve 36 closed, until it finally moves past the bottom opening 52 of the passage and moves into the cage 54. Once piston 48 moves out of the bottom opening 52 of passage 30, the pressure of the gel-like material tending to maintain the valve member 44 closed ceases and the pressure differential across the valve 36 is reversed, that is, the pressure of the cells acting on the bottom side of valve member 44 is greater than the pressure of the gel-like material on the top side of valve member 44. Under these conditions, the valve member 44 moves upwardly allowing the cellular phase to enter reservoir 34 and displace gel-like material 26 from the reservoir and passage 30 out into the liquid in tube 12. Preferably, the time-delay is sufficient to permit substantially complete phase separation, that is, long enough for substantially all of the cellular phase components to move to the lower end of the tube and below the upper end or passageway outlet 50. Since gel-like material 26 has a specific gravity intermediate the specific gravities of the separated low and high density blood phases, it moves toward the interface to form a complete partition or barrier such as indicated at 26' in FIG. 4. The barrier 26' extends in and about the upper end of the pipe 28 and forms a liquid-impervious barrier entirely across the interior of the tube. In FIG. 4, the piston 48 is shown in the cage 54 and it is apparent that once the piston passed the bottom opening 52 of passage 30, the gel-like material could freely move around the piston from the reservoir 34 and upwardly into passage 30 and eventually out the outlet 50. The cage 54 prevents the possibility of the piston 48 interfering with the valve member 44. The movable valve member 44 is shown in an open valve condition in FIG. 4. The low density serum or plasma phase is indicated at 58 in the upper portion of tube 12 in FIG. 4, while the high density cellular phase is indicated at 60, the two phases being separated by barrier 26'.

The barrier 26', because it was formed after a suitable time delay, does not trap cells in the low density phase 58. The barrier 26' permits the low and high phase densities to be stored without the high density contaminating the low density phase. The barrier also permits the device 10 to be shipped to a clinical laboratory where the low density phase, serum or plasma, may be decanted after removal of the stopper 20 without also decanting the cellular phase. The low density phase 58 may be removed in other ways where desired.

Referring now to FIGS. 5 and 6, a modified embodiment of a blood collection device in accordance with the present invention is indicated generally at 62. Device 62 is shown including a glass tube 64 integrally closed at the bottom by an integral bottom end portion 66 and closed at the upper open end by a stopper 68. Disposed in tube 64 is a blood phase partitioning device 70 which includes a housing 72 having a standpipe 74 and a stabilizing fin 76. The passageway has an open upper end or outlet 78 and a lower open end 80 in fluid communication with the interior of the tube 64. Pipe 74 provides a cylindrical passageway 82 which is closed at the upper open end 78 by a valve indicated generally at 84. Passageway 82 is filled with a thixotropic gel-like material 86. Disposed in passageway 82 is a cylindrical piston 87 having a specific gravity greater than that of the gel-like material, and preferably greater than that of the cellular phase of blood. Piston 87 may also be made of aluminum.

Valve 84 includes an elastomeric or rubber, movable valve member 88 which normally engages and sealingly closes the upper opening 78. Valve member 88 is connected to a stem 90 which has a horizontal stop member 92 connected at the bottom and which prevents the movable valve member 88 from leaving the pipe 74 by its engagement with an upper, in-turned portion of the pipe adjacent the upper opening 78. The stem and rod may be of plastic. The specific gravity of the housing 72 alone is made to be greater than that of the high density cellular phase to ensure that it remains in the bottom portion of tube 64. The specific gravity of valve member 88 should generally be greater than the low density phase and preferably greater than whole blood (about 1.05) but less than the high density phase. With the member 88 made to have a greater specific gravity than that of whole blood, it will not tend to rise when the tube 64 is filled with the blood sample. Because it has a specific gravity less than that of the cellular phase, it will readily move to open the valve once the piston 87 has moved below the passageway 82.

When it is desired to use the blood collection device illustrated in FIGS. 5 and 6, a blood sample may be introduced through the stopper 68 into the tube 64. Then, if it is desired to separate serum from the whole blood sample, the blood is allowed to coagulate. Thereafter, the device is placed in a centrifuge to separate and partition the phases.

During centrifugation, the piston 87 begins to move away from the upper end portion of passageway 82 and to move downwardly through the gel-like material 86. Because of the close fit between the piston 87 and inner walls of passageway 82, the gel-like material is squeezed past the piston at a relatively low flow rate so that the movement of the piston is retarded. The piston creates a pressure differential across it as well as across the valve member 88. This pressure differential causes the valve 84 to remain closed until the piston 87 moves outwardly beyond the lower open end 80 of the passage 82, such as shown in FIG. 6. When piston 87 moves below the open end 80, the pressure differential that had been present across the piston and valve 84 ceases, and the pressurized cellular phase now enters the lower end opening 80 to move the gel-like material 86 upwardly in passage 82 and to open valve 84, that is, move the valve member 88 upwardly, such as to the position shown in FIG. 6. The gel-like material, having a specific gravity intermediate those of the low density and high density phases indicated at 94 and 96, respectively, in FIG. 6, now flows to the interface to form a complete barrier 86' across the interior of the tube 64 between the separated phases.

In FIG. 6, the piston is shown at the bottom of the tube 64, and the passageway 82 substantially filled with the cellular phase. The gel-like material of barrier 86' fills the upper end portion of passageway 82 and is in and about the valve 84 and pipe 74 to form a complete liquid-impervious seal between the phases.

In FIG. 7, still another embodiment of a blood collection device in accordance with the present invention is indicated at 100. Device 100 includes a blood collection tube 102 integrally closed at the lower end and having a stopper 106 closing the upper end of the tube. A blood phase partitioning device 108 is disposed within tube 102 adjacent the lower end portion. Partitioning device 108 includes a housing 109 having a pipe 110 providing a passage 112 filled with gel-like material 114. The pipe 110 is integrally connected at the bottom to a cup-shaped, resilient sealing piston 116 which sealingly engages the inner walls of the tube 102. Gel-like material 114 not only fills the passage 112 but also the space between the cup-shaped piston 116 and the inner surface of the bottom 104 of tube 102. The partitioning device 108 also includes a piston 118 sized to be in relatively close fitting relation with the inner walls of passageway 112 and which is located initially adjacent the upper open or outlet end 120 of passageway 112. The passageway 112 has an opening 121 at its lower end. The partitioning device 108 further includes an integral spacing rod 122 which extends upwardly to a point just below the bottom surface of stopper 106.

In employing collection device 100, blood is introduced through the stopper 106 into the interior of the tube 102. The device is subsequently placed in a centrifuge and centrifugation started. Piston 118, under the influence of centrifugal forces, begins moving downwardly in passage 112. During downward movement of piston 118, a pressure differential is created across the piston as the piston pressurizes the gel-like material 114 below it. This pressure differential prevents gel-like material from flowing out of outlet opening 120. Because the gel-like material 114 is pressurized, there is a tendency of the housing 109 to move upwardly since the material cannot flow past the periphery of the cup-shaped piston 116, however, the housing is prevented from doing so by rod 122 which would engage the stopper 106. During continued centrifugation, the cellular phase moves downwardly applying pressure to the upper side of cup-shaped piston 116. However, the pressurization of the gel-like material by piston 118 is sufficiently great to prevent the downward movement of cup-shaped piston 116 until piston 118 falls below and out of opening 121 of the passage 112, such as to the position shown in phantom. Once the pressure differential across the piston is removed, that is, when the piston 118 falls below the opening 121, the centrifugal forces acting on the cellular phase and the housing 109 urge the cup-shaped piston 116 downwardly into the gel-like material with the material rising in passage 112 and moving out of the outlet end 120 of the passage. The gel-like material 114 then flows to the interface between the two separated phases to form a phase partition or barrier such as shown in phantom at 114'. The barrier 114' will fill the upper end of pipe 110 and extend around the pipe to completely seal off the separated phases from each other.

The cup-shaped piston 116 and rod 122 in the embodiment shown in FIG. 7 serve to not only block or prevent gel-like material from flowing out the housing 109, such as past the periphery of piston 116, until after the piston 118 has dropped out of the bottom opening 121 of the passageway 112, but also serve as a piston to urge the gel upwardly and out of the partitioning device toward the phase interface. The housing 109 alone preferably is made, for example, of a filled plastic, such that it has a specific gravity greater than that of the cellular phase.

In each of the illustrated embodiments, the pipe is shown long enough to locate the outlet or upper end opening of the pipe or passageway in the low density zone of the tube. That is, the outlet is positioned in that part of the tube which will contain the low density phase after complete phase separation. Preferably, and as shown in the drawings, the outlet is above the interface of the phases so that the gel-like material flows out of the pipe and then back down toward the interface. This even further ensures that any slow-to-descend cells will be covered by at least the last portion of the gel-like material forming the phase barrier. Also, since the gel-like material flows in the pipe or passageway while in the cellular phase, it does not engage the cellular phase components or carry cells with it to the interface. Utilizing the piston and passageway to obtain a time delay as described, results in excellent cell-free, high quality serum or plasma.

The specific gravity of the piston 48, 87 or 118, the viscosity of the gel-like material and the relative sizes or diameters of the piston and passageway primarily will determine the length of the time delay for a given number of units of gravity produced by the centrifuge. Generally, a time delay of one minute is helpful. Preferably, a time delay of two or more minutes is preferred. Where the speed of the centrifuge is relatively low, the centrifugal forces acting on the piston will be less and the time necessary for it to traverse the passageway will be longer to provide a longer time delay which is desirable since the time necessary for phase separation will also be longer. Where the speed of the centrifuge is relatively high, the time delay will automatically be less and this is desirable because the phase separation time will also be less. Thus, the time delay obtained will tend to compensate for variations in centrifuge speed where centrifuges of various speeds are employed.

As various changes could be made in the above-described construction without departing from the scope of the invention, it is intended that all matter contained in the above description and shown in the accompanying drawings be interpreted as illustrative and not in a limiting sense.

We claim:

1. A blood collection device for receiving whole blood adapted to be centrifugally separated and partitioned into relatively low and high density phases comprising a container for receiving a blood sample having an open upper end and a closed lower end, a stopper closing said upper end, and a blood phase partitioning device in said container including a housing having an elongated passageway therein with a lower opening spaced from but adjacent said lower end of said container and an upper outlet opening spaced from said lower end of said container, flowable thixotropic gel-like material disposed in said housing including said passageway between said lower and upper openings thereof and having a specific gravity intermediate those of the relatively low and high density phases of blood and flowable from said upper outlet opening during centrifugation of the device to form a phase barrier between the separated phases, and time delay means for delaying the initiation of the flow of said gel-like material from said outlet opening including movable means disposed in said passageway and spaced from said lower opening and having a specific gravity greater than that of said gel-like material, said movable means being movable in said passageway toward said lower opening and being sized relative to the size of said passageway to allow restricted flow of said gel-like material past said movable means and to retard the movement of said movable means in said passageway during centrifugation of the device, and means for preventing the flow of said gel-like material from said housing during movement of said movable means to said lower opening of said passageway, said movable means being movable beyond said lower opening of said passageway to permit flow of said gel-like material upwardly in said passageway and out of said upper outlet opening to form a phase barrier between the separated phases.

2. The device of claim 1 wherein said means for preventing the flow of said gel-like material from said housing includes normally closed valve means between the interior of said housing and the interior of said container exteriorly of said housing responsive to the movement of said movable means beyond said lower opening of said passageway to open and allow said gel-like material to flow out of said outlet opening.

3. The device of claim 2 wherein said valve means is disposed below said lower opening of said passageway.

4. The device of claim 3 wherein said valve means includes an opening in said housing, and a movable valve member normally closing said opening and having a specific gravity greater than that of said gel-like material.

5. The device of claim 2 wherein said valve means is disposed above said outlet opening and said movable means.

6. The device of claim 5 wherein said valve includes a movable valve member normally closing said outlet opening of said passageway and having a specific gravity greater than that of whole blood.

7. The device of claim 6 wherein said movable valve member has a specific gravity less than that of the separated high density phase.

8. The device of claim 4 or 6 wherein said movable means effects a pressure differential across said valve member to maintain said valve closed until said movable means moves beyond said lower opening.

9. The device of claim 1 wherein said housing includes a movable member connected to the lower end of said passageway in spaced relation from the bottom of said container and having a resilient periphery sealingly engaging the inner sidewalls of said container, said gel-like material filling the space between said movable member and the bottom of said container, said movable member being movable downwardly during centrifugation of the device after said movable means moves beyond said lower opening to effect pressurization of said gel-like material upwardly in said passageway and through said outlet opening, and means on said movable member preventing movement of said housing upwardly in said container during downward movement of said movable means in said passageway.

10. The device of claim 9 wherein said means on said movable member includes an extension of said housing extending therefrom to a point adjacent said stopper to limit upward movement of said housing.

11. The device of claim 1 wherein said housing is substantially stationary with respect to said container.

12. The device of claim 1 or 11 wherein said housing without said movable means has a specific gravity greater than that of the high density phase.

13. The device of claim 1 wherein said lower opening is in direct fluid communication with the interior of said container exteriorly of said housing.

14. The device of claim 1 wherein said movable means comprises a piston means slidable in said passageway.

15. A blood collection device for receiving whole blood adapted to be centrifugally separated and partitioned into relatively low and high density phases comprising a container for receiving a blood sample having an open upper end and a closed lower end, a stopper closing said upper end, and a blood phase partitioning device in said container including a housing having an elongated passageway therein with a lower opening spaced from but adjacent said lower end of said container and an upper opening spaced from said lower end of said container, flowable thixotropic gel-like material disposed in said passageway between said lower and upper openings thereof and having a specific gravity intermediate those of the relatively low and high density phases of blood and flowable from said outlet opening during centrifugation of the device to form a phase partition between the separated phases, piston means disposed in said passageway and spaced from said lower opening and having a specific gravity greater than that of said gel-like material, and normally closed valve means normally having opposed sides thereof respectively in fluid communication with said gel-like material and the interior of said container, said piston means being movable in said passageway toward said lower opening in response to centrifugation of said device, said piston means being sized relative to said passageway to allow restricted flow of said gel-like material past said piston means and to retard the movement of said piston means in said passageway during centrifugation of the device to effect a pressure differential across said piston means and said valve means to prevent the flow of said gel-like material from said upper opening, said piston means being movable beyond said lower opening during centrifugation of the device to eliminate the pressure differential across said piston means and valve means to permit the flow of said gel-like material out of said upper opening and to form a phase barrier between the separated phases.

16. A blood collection device for receiving whole blood adapted to be centrifugally separated and partitioned into relatively low and high density phases comprising a container for receiving a blood sample having an open upper end and a closed lower end, a stopper closing said upper end, and a blood phase partitioning device in said container including a housing having an elongated passageway therein with a lower opening adjacent but spaced from said lower end and an upper opening spaced from said lower end, flowable thixotropic gel-like material disposed in said passageway between said lower and upper openings thereof and having a specific gravity intermediate those of the relatively low and high density phases of blood and flowable from said upper opening during centrifugation of the device to form a phase partition between the separated phases, and time delay means for delaying the initiation of the flow of said gel-like material from said outlet opening including piston means disposed in said passageway and spaced from said lower opening and having a specific gravity greater than that of said gel-like material, said piston means being movable in said passageway toward said lower opening in response to centrifugation of said device, said piston means being sized relative to said passageway to allow restricted flow of said gel-like material past said piston means and to retard the movement of said piston means in said passageway during centrifugation of the device to pressurize said gel-like material in said passageway, and valve means responsive to the pressurization of said gel-like material to prevent the flow of said gel-like material from said upper opening, said piston means being movable beyond said lower opening during centrifugation of the device to decrease the pressurization of said gel-like material to actuate said valve means to permit the flow of said gel-like material out of said upper opening and to form a phase barrier between the separated phases.

17. The device of claim 14, 15 or 16 wherein said piston means has a specific gravity greater than that of the separated high density phase.

* * * * *